United States Patent [19]

Palumbo

[11] 4,296,744
[45] Oct. 27, 1981

[54] DYNAMIC PATELLAR BRACE

[76] Inventor: Pasquale M. Palumbo, 906 Frome La., McLean, Va. 22101

[21] Appl. No.: 153,708

[22] Filed: May 27, 1980

Related U.S. Application Data

[63] Continuation of Ser. No. 949,121, Oct. 6, 1978, abandoned.

[51] Int. Cl.³ .............................................. A61F 3/00
[52] U.S. Cl. ................................. 128/80 C; 128/165; 2/24
[58] Field of Search ................... 128/80 C, 87 R, 165; 2/22, 24

[56] References Cited

U.S. PATENT DOCUMENTS

| | | | |
|---|---|---|---|
| 1,388,772 | 8/1921 | Sheehan | 128/165 |
| 2,220,836 | 11/1940 | Closson | 128/165 |
| 2,270,685 | 1/1942 | Miller | 128/165 |
| 3,046,981 | 7/1962 | Biggs, Jr. et al. | 128/80 C |
| 3,804,084 | 4/1974 | Lehman | 128/80 C |
| 3,945,046 | 3/1976 | Stromgren | 128/80 C |
| 4,084,584 | 4/1978 | Detty | 128/80 C |
| 4,116,236 | 9/1978 | Albert | 128/80 C |

FOREIGN PATENT DOCUMENTS

| | | | |
|---|---|---|---|
| 840438 | 4/1939 | France | 128/165 |
| 16032 | 7/1898 | United Kingdom | 128/165 |

*Primary Examiner*—Robert W. Michell
*Assistant Examiner*—Arthur S. Rose
*Attorney, Agent, or Firm*—Paul S. Richter

[57] ABSTRACT

A dynamic patellar brace useful for both diagnosis and treatment of patellar subluxation. The patellar brace includes a patellar bracing pad adapted to be positioned laterally with respect to the patella and to apply medial pressure to the patella to prevent subluxation for all normal ranges of knee flexion and motion. The patellar brace may be used to facilitate positive diagnosis of patellar subluxation whose symptoms may mimic other pathological problems of the knee and, therefore, lead to an erroneous diagnosis. The brace may also be used for treatment and/or to delay or avoid the need for corrective surgery.

12 Claims, 4 Drawing Figures

DYNAMIC PATELLAR BRACE

This is a continuation of application Ser. No. 949,121 filed Oct. 6, 1978, now abandoned.

BACKGROUND OF THE INVENTION

The present invention relates to knee support devices, and more particularly to a dynamic patellar brace or splinting device intended to stabilize the patella to prevent patellar subluxation during all normal degrees of knee flexion and motion.

It is well-known that loosely ligamented individuals, as well as individuals with certain peculiar anatomic features of certain components of the knee, frequently develop various pathological problems with their knees, particularly when these individuals are active in physically strenuous activities, such as athletic activities. The most commonly occurring problems relate to stretching or tearing of the various knee ligaments, injury to the cartilage (meniscal) and articular surfaces of the knee joint, and fractures. Patellar subluxation or abnormal and undesirable movement of the patella, laterally, relative to its normal up and down movement in the vertical track defined by the trochlea can precipitate the onset of chondromalacia or aggravate existing chondromalacia of the patella, as well as cause diagnostic problems of the knee.

Subluxation of the patella can be caused by certain developmental abnormalities of the skeletal components of the knee and/or the presence of musculaligamentous laxity or dysplasia. The patella may leave its normal, vertical tracking groove as a result of abnormal vector forces and/or by passive lateral or rotary forces. The abrupt abnormal lateral displacement of the patella from its groove during any weight bearing activity (such as running, stair climbing, etc.) frequently results in immediate, temporary disability (such as buckling of the knee), causing a subjective sensation in the knee similar to that caused by other unrelated pathological conditions within the knee.

The sensation of pain and/or imminent buckling of the knee results in apprehension and restriction of certain weight bearing activities such as athletic endeavors. The resultant increased abnormal traction forces on the peripatellar soft tissues frequently lead to inflammatory changes of the retinaculae, patellar ligament and/or tendon (tendinitis).

Furthermore, the repetitive, abnormal lateral excursions which cause abnormal shearing forces, frequently lead to early, accelerated and progressive degenerative changes (chondromalacia) of the patella and femoral condyles.

As noted above, problems peculiar to the patella compromise only a portion of all common physiological problems of the knee and several, unrelated or partially related problems may occur simultaneously, particularly in individuals having loose ligaments or when engaged in relatively strenuous activities involving the knee. Physicians generally, and orthopedic surgeons in particular, have only recently begun to fully appreciate the frequency and importance of patellar subluxation in the context of overall knee problems. Accordingly, the diagnosis of patellar subluxation may be difficult to ascertain using conventional techniques, especially because other problems with the knee frequently cause subjective symptoms similar to those of subluxation of the patella.

Not only may the proper diagnosis of patellar subluxation, particularly in its milder form, be difficult using conventional techniques, but even when properly diagnosed, the preferred treatment may be somewhat limited. For example, young children still in the active bone growth phase of life frequently are relatively loosely ligamented and suffer from various degrees of patellar subluxation. However, it is well recognized that it is preferable to avoid or delay corrective surgery for such individuals, if at all possible, until such individuals reach a more physiologically opportune age when their growth plates have closed.

Others have devoted attention and proposed various knee braces and supports directed to general problems of the knee. For example, Spiro, U.S. Pat. No. 3,473,527; Lehman, U.S. Pat. No. 3,804,084, and Moore, U.S. Pat. No. 3,853,123, have proposed various knee support, brace, and knee splinting devices intended to restrain the knee to prevent normal knee flexion or movement. Such devices are directed, generally, to the problem of immobilizing the knee as a whole, and do not provide dynamic patellar bracing during normal knee flexion and extension. Nirschl, U.S. Pat. No. 3,926,186 and Stromgern, U.S. Pat. No. 3,945,046, propose other muscular and flexible knee supports. Nirschl's apparatus, however, is not designed to provide medial-lateral stabilization of the patella, and is inherently incapable of performing a dynamic bracing function for the patella. Stromgern's apparatus, on the other hand, is not concerned with patellar stabilization, but instead is directed to the general problem of providing stability to the medial knee ligament complex.

Detty, U.S. Pat. No. 4,084,585 discloses a simple knee sleeve device which includes a pad and which is capable of providing limited, static patellar bracing when the knee is passive, i.e., not in motion or when in a single position or a narrow range of positions.

SUMMARY OF THE INVENTION

Accordingly, an object of the present invention is to provide a dynamic patellar brace useful both for diagnosis and treatment of patellar subluxation, and certain physiological problems of the knee related to or aggravated by patellar subluxation.

A still further object of the invention is to provide a dynamic patellar brace capable of performing its bracing or splinting function for the patella during the full, normal range of knee flexion and movement.

A still further object of the invention is to provide a dynamic patellar brace to facilitate proper and positive diagnosis of patellar subluxation, particularly in its milder form when its clinical presentation simulates that of other pathological conditions of the knee.

A still further object of the present invention is to provide a dynamic patellar brace suitable for use in children having patellar subluxation but whose growth plates are still open, so as to delay or avoid the need for corrective surgery until a more physiologically opportune time is reached.

A still further object is to provide a dynamic patellar brace offering other treatment advantages.

A still further object of the invention is to provide a patellar brace which is relatively simple to put in place and which will provide dynamic patellar bracing without need for constant adjustment or re-adjustment.

A still further object of the invention is to provide a dynamic patellar brace which can be utilized with minimal discomfort, without being unsightly, and without requiring the user to utilize crutches or to walk in an unnatural manner.

A still further object of the invention is to provide a dynamic patellar brace having a relatively simple construction, and which is relatively simple to manufacture.

Toward the fulfillment of these and other objects, the present invention includes a patellar bracing pad and dynamic means for positioning said pad laterally of the patella and causing the patellar pad to apply medial pressure to the patella during all normal degrees of knee flexion and movement to prevent patellar bracing pad subluxation. The patella is preferably attached to an elastic sleeve adapted to have the leg inserted therethrough and to have the knee positioned therein. Two elastic, dynamic arms attached to the patellar bracing pad are adapted to be wrapped circumferentially in a first direction about the leg to cause the pad to apply medial pressure to the patella. An elastic, dynamic counterarm, also attached to the pad, is adapted to be wrapped circumferentially in a direction opposite to the first direction to stabilize the patellar brace throughout the normal range of knee flexion and movement.

DESCRIPTION OF THE PREFERRED EMBODIMENTS

Figure 1:
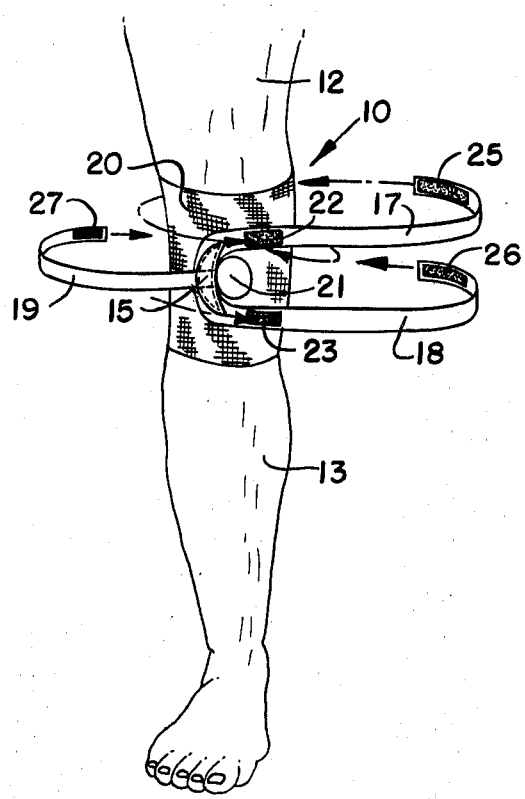
FIG. 1 is a perspective view of the dynamic patellar brace according to the present invention positioned on the knee and ready to have the elastic arm and counterarm members thereof wrapped circumferentially about the knee.

As shown in FIG. 1, a dynamic patellar brace 10 according to the present invention is positioned on the knee between the upper portion 12 and lower portion 13 of the leg of the user (not shown). The patellar brace includes an elastic sleeve 20 through which the lower portion 13 of the user's leg has been inserted to facilitate positioning of a patellar bracing pad 15 laterally of the patella (not shown) of the user's knee. The elastic sleeve 20 includes an aperture 21 which is preferably positioned over or about the patella or knee cap by feel when the leg is inserted through the elastic sleeve 20.

As further shown in FIG. 1, the dynamic patellar brace includes two elastic arm members 17, 18 adapted to be wrapped circumferentially in a first direction, counter-clockwise as shown in FIG. 1, when in the brace in use. Each of the elastic arm members 17, 18 is attached to the patellar bracing pad 15, and arranged so that when circumferentially wrapped in the first direction about the user's knee when the brace is in use, the bracing pad 15 will thereby cause pressure to be applied medially to the user's patella.

The arm members 17 and 18 include thereon fastening and holding means 22 and 23, respectively, which preferably comprise Velcro strip means attached to the elastic arm members 17, 18 along the outer band surfaces thereof at positions near to the points at which the arm members 17, 18 are attached to the patellar bracing pad 15. Cooperating fastening and holding means 25, 26 associated respectively with the elastic arm members 17, 18 are attached to the inner band surfaces thereof, respectively, near the ends thereof furthest removed from the point of attachment to the patellar bracing pad 15.

The patellar brace 10 also includes a dynamic elastic counterarm 19 having one end thereof also attached to the patellar bracing pad 15, and the other end thereof adapted to be wrapped circumferentially in a direction opposite to the first direction, clockwise in FIG. 1, about the user's knee. A fastening and holding means 27, preferably also a Velcro strip means, is attached to the inner band surface of the elastic arm member 19 as shown.

Figure 2:
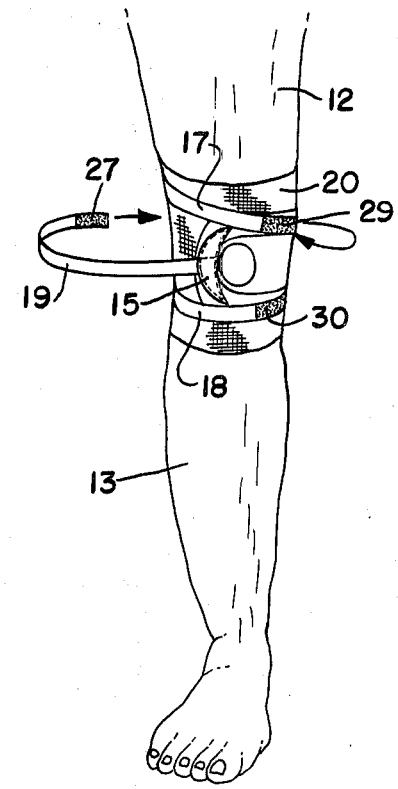
FIG. 2 is a perspective view similar to FIG. 1 but showing the two elastic arm members circumferentially wrapped, and with the counterarm member ready to be circumferentially wrapped about the knee.

FIG. 2 is a view similar to FIG. 1, but illustrates the patellar brace 10 with the first and second elastic arm members 17, 18 thereof circumferentially wrapped about the user's knee and fastened and held in the wrapped position. The fastening means 25 engages with the fastening means 22 on the arm member 17, and the fastening means 26 engages with the fastening means 23 on the arm member 18 to hold the arm members 17, 18 in the wrapped position. It is noted that the first arm member 17 is wrapped circumferentially about the knee above the patella, and the second arm member 18 is wrapped circumferentially about the knee below the patella. This arrangement causes each of the arm members 17 and 18 to exert pressure in the medial direction (i.e., toward the center-line of the user) on the patellar bracing pad 15 to cause the patellar bracing pad 15 positioned laterally of the patella to thereby apply medial or inwardly directed pressure to the patella to prevent patellar subluxation.

As further shown in FIG. 2, fastening or holding means 29, 30, preferably also Velcro strip means, are attached to the ends, respectively, of the arm members 17, 18, at the ends thereof furthest removed from the patellar bracing pad 15, on the outer band surfaces thereof. These fastening and holding means 29, 30 are adapted to cooperate with the fastening and holding means 27 on the inner surface of the counterarm member 19 as will be further described.

Figure 3:
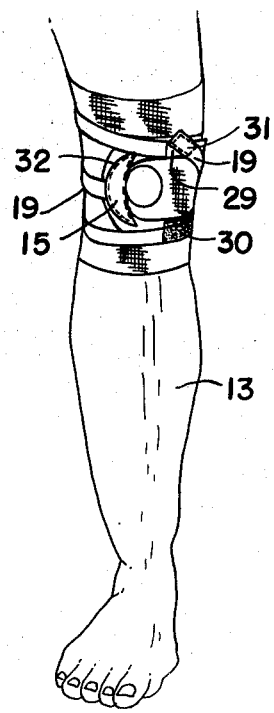
FIG. 3 is a further perspective view similar to FIG. 2 but showing all of the elastic arm and counterarm members wrapped and held in the wrapped position.

FIG. 3 is a view similar to FIG. 2, but showing the elastic counterarm member 19 now circumferentially wrapped in the clockwise direction with the end thereof furthest from the patellar bracing pad 15 fastened and held by cooperation between the fastening means 27 and the fastening means 29 previously described. It is noted it would be possible to fasten the end of the counterarm member 19 circumferentially wrapped about the knee by cooperation between the fastening means 27 and the fastening means 30 associated with the lower arm member 18 instead of with the fastening means 29 associated with the upper arm member 19. In either case, the counterarm member 19 serves to dynamically stabilize the position of the patellar bracing pad on the knee.

In a preferred embodiment, either of the fastening means 29 or 30 is capable of cooperating with the fastening means 27 to hold the counterarm member 19 in the wrapped position. This arrangement facilitates wrapping and fastening of the counterarm member as the person initially applying the brace to the user may choose to fasten the end of the counterarm member 19 furtherest from the patellar bracing pad either to the upper or to the lower arm member 18 or 19. The precise point at which the counterarm member is fastened and held generally makes little or no difference to the user. This arrangement also permits the use of a single brace for either the left or the right knee of a user as it allows the upper and lower portions of the brace to be mirror images of each other.

It is also seen from FIG. 3 that the fastening or holding means 27, preferably a Velcro strip means, is fastened to the end of the counterarm 19 furthest from the patellar bracing pad 15 by stitching means 31. The other fastening or holding means 22, 23, 25, 26, 29 and 30 may also be fastened to the elastic band members by similar stitching means (not shown) or by other appropriate adhesive or epoxy means.

Figure 4:
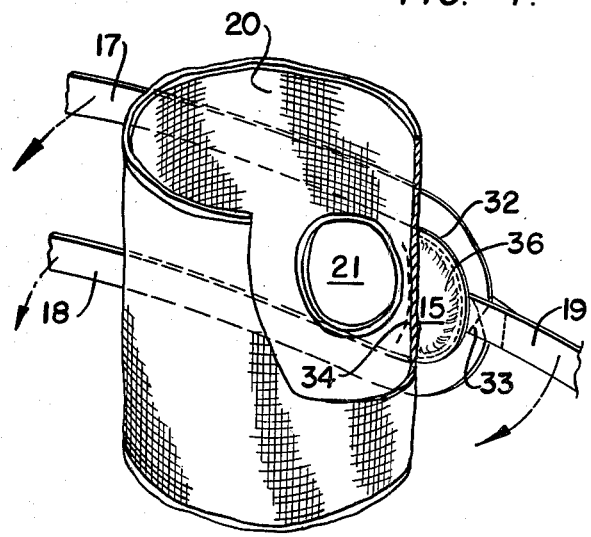
FIG. 4 is a perspective view, partially fragmentary, illustrating further details of a patellar brace according to the present invention.

FIG. 4 illustrates further details of the elastic sleeve member 20 and the connection and attachment thereto of the patellar bracing pad 15, and the attachment of the arm members 17 and 18 and the counterarm member 19 thereto and to the pad 15. As shown in FIG. 4, the elastic sleeve member 20 preferably comprises a sleeve of elastic material having an approximately circular aperture 21 therein. The lower 13 leg of the user of the patellar brace may be inserted through the elastic sleeve 20 so that his or her knee cap or patella is positioned within the sleeve 20 in registration with the circular aperture 21. This can be readily accomplished by manually feeling the position of the patella or the knee cap, and making sure that the patella is initially moved to its normal up and down vertical track defined by the trochlea. Then, by assuring that the aperture 21 of the sleeve 20 is positioned over the patella, the user of the brace automatically obtains proper positioning of the patellar bracing pad 15 laterally of his or her patella. The user, of course, must be sophisticated enough to realize that the patellar bracing pad 15 is to be positioned laterally of the patella. Thus, the user must insert his leg through a different end of the elastic sleeve 20 depending upon whether the brace 10 of FIGS. 1–3 is to be used on his or her left or right knee. It would, of course, be possible to mark the ends of the sleeve 20 for left knee or right knee use.

In a preferred embodiment the diameter of the elastic sleeve member and the elastic material and forces thereof are selected so as to not unduly constrict the blood flow within the leg or knee of the user. Preferably, a series of different sized braces must be provided to accommodate different users. Although a primary purpose of the sleeve 20 and the aperture 21 therein is to permit a relatively unskilled user of the brace to achieve accurate alignment of the patellar bracing pad relative to the patella, the elastic sleeve member 20 also inhibits sliding movement of the brace about the knee. However, it is the arrangement, wrapping, and fastening of the arm 17, 18 and counterarm 19 members circumferentially about the knee which primarily causes the patellar bracing pad 15 to be maintained in position laterally of the patella and to provide medially directed pressure thereto throughout the normal range of knee flexion and movement.

It should also be noted that the patellar bracing pad 15 is arcuately shaped, concave toward the aperture 21 which is adapted to be positioned over the patella when the patella is initially in its normal vertical track defined by the trochlea when the brace is first applied. It is also seen from FIG. 4 which shows the underside of the patellar bracing pad 15 that the pad 15 preferably has a thickness of elevation 36 to it, and is preferably formed from a partially resilient, padding material adapted to permit the pad 15 to contour itself to the patella against which it applies medially directed forces. The patellar bracing pad 15 is also preferably attached to the sleeve 20 by stitching means 34.

As further shown in FIG. 4, the upper and lower arm members 17 and 18 and the counterarm member 19 may also be attached to the patellar bracing pad 15 by appropriate stitching means 32, 33. The upper and lower elastic arm members 17 and 18 can be constructed from a single U-shaped piece of elastic band or rubber material and attached by stitching means 32, 33 to the bracing pad 15. This arrangement facilitates development of uniform medially directed forces in the bracing pad 15 when the elastic arm members 17, 18 are circumferentially wrapped about the knee as previously described. The elastic counterarm 19 is also preferably constructed from an elastic band or rubber material and is preferably attached to the bracing pad 15 at the vertical midpoint thereof by stitching means 33.

It may also be seen that the arcuately shaped bracing pad 15, concave towards aperture 21 (i.e., towards the patella) will tend to dynamically confine the patella to its normal up and down movement in the vertical track defined by the trochlea. In particularly, during full flexion or bending of the knee, the upper and lower portions of the bracing pad 15 will bend with the knee and provide pressure surfaces to continuously provide medial pressure against the patella to prevent subluxation in the lateral direction. As previously noted, subluxation of the patella can only occur in the lateral or outwardly moving direction on each knee, and it is only necessary, therefore, to provide a dynamic, lateral restraint to prevent such subluxation.

It may now be seen that the dynamic patella brace 10 of the present invention may be advantageously used to prevent patellar subluxation in the user during all normal degrees of knee flexion and movement. Unlike prior art devices, the combination of the elastic sleeve 20, the circumferentially wrapped arms 17, 18 and the circumferentially wrapped counterarm 19 cause the patellar bracing pad 15 to be maintained in proper position laterally of the patella during all normal degrees of knee flexion and motion and to apply medially directed pressure to the patella of the user to prevent subluxation.

As noted previously, a dynamic patellar brace according to the present invention may be advantageously employed for diagnosis of patellar subluxation difficulties of the knee, particularly when patellar subluxation presents in its milder form and/or its symptoms simulate those of other pathological conditions of the knee. For purposes of diagnosis, the patellar brace may be applied by the physician or Orthopedic Surgeon to the patient suspected of having a patellar subluxation problem with instructions to the patient to wear the brace for a relatively short period of time and to perform a series of diagnostic test exercises. Such test exercises may include ascending and descending stairs or pivoting on the involved extremity while running. At the conclusion of such series of diagnostic test exercises, the patient will be requested to state whether he or she noticed reduced pain or increased stability of the knee during such exercises. If the patient reports such an improvement, the physician may conclude that patellar subluxation is at least a contributing factor, if not the causative agent, in the patient's knee difficulties or complaints.

In cases in which patellar subluxation problems are diagnosed, the dynamic patellar brace according to the present invention may then also be used for treatment purposes. For example, in young children still in the active bone growth phase of life, the wearing of a dynamic patellar brace according to the present invention will prevent patellar subluxation and related problems, and allow corrective surgery to be postponed or avoided. It is well known that surgery is preferably avoided, if at all possible, in relatively young children because disturbance of the growth plates in such children, which may accidentally occur, can result in uneven bone growth rates and possible deformity after surgery. It is also well known that relatively loose ligaments occur more often in younger persons and that the musculoligamentous structures tend to become tighter with advancing age. Thus the patellar brace, according to the present invention, may be advantageously used in younger persons in that it may obviate the need for future surgical intervention in certain milder forms.

It is also believed that dynamic patellar braces according to the present invention are useful for treating patellar subluxation by simply preventing further stretching of the ligaments. With repeated subluxation, the medial ligament of the patellae (retinaculum) becomes stretched and the lateral ligament (retinaculum) tightens, tending to more readily permit further subluxation occurrences. If the patellar brace according to the present invention is utilized, however, the patella will be confined to its normal up and down vertical track defined by the trochlea, and, therefore, prevent the development of or stretch an already tight lateral retinaculum. Thus, the need for corrective surgery may be avoided.

It is also believed that the patellar stabilizing brace may be useful in certain forms of isolated patellofemoral chondromalacia by changing apposing contact or pressure points which are frequently painful.

Accordingly, it is seen that the dynamic patellar brace according to the present invention accomplishes the above described objects as well as other objects which will be apparent to those skilled in the art. It will further be apparent to those skilled in the art that various modifications and changes may be made to the present invention without departing from the scope of the invention as defined in the appended claims.

What is claimed is:

1. A dynamic patellar brace for preventing subluxation of a patella throughout the complete physiologic range of flexion and movement of the knee comprising:
   means for bracing the patella;
   means for maintaining said patellar bracing means positioned laterally of the patella throughout the complete physiologic range of flexion and movement of the knee when the brace is in use; and
   means for causing said patellar bracing means positioned laterally of the patella to apply a resultant force in the medial direction to the patella throughout the complete physiologic range of flexion and movement of the knee when the brace is in use.

2. A dynamic patellar brace according to claim 1:
   wherein said means for causing said patellar bracing means to apply pressure comprises first and second elastic arm members, the first end of each of which is adapted to be circumferentially wrapped in a first direction about the knee when the brace is in use; and
   wherein said means for maintaining said patellar bracing means positioned comprises an elastic counterarm member, the first end of which is adapted to be circumferentially wrapped in a direction opposite to the first direction about the knee when the brace is in use.

3. A dynamic patellar brace according to claim 1 or 2 wherein the medial side of said patellar bracing means positioned laterally of the patella when the brace is in use is arcuately shaped, concave towards the patella.

4. A dynamic patellar brace according to claim 2 wherein said first and second elastic arm members are adapted to be circumferentially wrapped about the knee above and below the patella, respectively, when the brace is in use.

5. A dynamic patellar brace according to claim 4 wherein the medial side of said patellar bracing means positioned laterally of the patella when the brace is in use includes means which are arcuately shaped, concave towards the patella.

6. A dynamic patellar brace according to claims 2, 4 or 5 further comprising means operably associated with said first and second arm members and with said counterarm member and adapted to hold the second ends of said circumferentially wrapped members to prevent the unwrapping of said members when the brace is in use.

7. A dynamic patellar brace according to claims 1, 2, 4 or 5 further comprising an elastic sleeve attached to said patellar bracing means and adapted to have the knee positioned substantially within said sleeve when the brace is in use.

8. A dynamic patellar brace for preventing subluxation of a patella throughout the complete physiologic range of flexion and movement of the knee comprising;
   pad means for placement laterally adjacent of the patella for laterally stablizing the patella throughout the physiologic range of flexion and movement of the knee;
   force developing means connected to said pad means for applying a force thereto, said pad means coupled with said force developing means applying a resultant force in the medial direction to the patella throughout the complete physiologic range of flexion and movement of the knee when the brace is in use, said force developing means including first and second elastic bands wrapped in a first circumferential direction about the leg, one of said elastic bands wrapped above the knee and the other wrapped below the knee; and
   position maintaining means connected to said pad means for maintaining the position of said pad relative to the patella throughout the physiologic range of flexion and movement of the knee and including a third elastic band wrapped about the leg in a second circumferential direction, said third elastic band intermediate said first and second elastic bands.

9. A dynamic patellar brace for preventing subluxation of a patella throughout the complete physiologic range of flexion and movement of the knee comprising:
   padded means for placement adjacent of the patella for positionally stablizing the patella throughout the physiologic range of flexion and movement of the knee;
   force developing means coupled to said padded means for applying a force thereto, said padded means coupled with said force developing means applying a resultant force in the medial direction to the patella throughout the complete physiologic range of flexion and movement of the knee when the brace is in use, said force developing means including first and second elastic bands wrapped in a first circumferential direction about the leg, one of said elastic bands wrapped above the knee and the other of said elastic bands wrapped below the knee; and position maintaining means coupled to said padded means for maintaining the position of said padded means relative to the patella throughout the complete range of physiologic flexion and movement of the knee and including a third elastic band wrapped about the leg in a second circumferential direction, said third elastic band intermediate said first and second elastic bands.

10. A dynamic patellar brace for preventing subluxation of a patella throughout the complete physiologic range of flexion and movement of the knee comprising:

a tubular sleeve formed from an elastomer material having an opening formed in the wall portion thereof intermediate its ends and defining padded means laterally adjacent the opening, said sleeve positionable on a leg with the patella in registration with the opening therein and the padded means positioned laterally adjacent the patella;

force developing means coupled to said padded means for applying a force thereto, said padded means applying a resultant force in the medial direction to the patella throughout the physiologic range of flexion and movement of the knee, said force developing means including first and second elastic bands wrapped in a first circumferential direction about the leg, one of said elastic bands wrapped above the knee and the other of said elastic bands wrapped below the knee; and position maintaining means coupled to said padded means for maintaining the position of said padded means relative to the patella throughout the range of physiologic flexion and movement of the knee and including a third elastic band wrapped about the leg in a second circumferential direction, said third elastic band intermediate said first and second elastic bands.

11. A dynamic patellar brace for preventing subluxation of a patella throughout the complete physiologic range of flexion and movement of the knee comprising:

a tubular sleeve formed from an elastomeric material having an opening formed in a wall portion thereof intermediate its ends and defining padded means laterally adjacent the opening, said sleeve positionable on a leg with the patella in registration with the opening thereof and said padded means positioned laterally adjacent the patella;

force developing means coupled to said padded means for applying force to the patella to effect lateral stabilization, said force developing means including first and second straps connected at their proximate ends through a connecting portion that is coupled to said padded means, said first and second elastomeric straps wrapped in a first circumferential direction about the leg, one of said elastomeric straps wrapped above the knee and the other of said elastomeric straps wrapped below the knee; and a position stablizing strap for stablizing the position of the force developing means throughout the range of physiologic flexion and movement of the knee and including a third elastomeric strap wrapped about the knee in a second circumferential direction, the proximate end of said third elastomeric strap connected to said connecting portion intermediate said first and second strap.

12. The dynamic patellar brace claimed in claims 8, 9, 10 or 11 wherein each of said first, second, and third elastic bands includes a remote end having a detachable attaching means; the remote end of said first elastic band detachably attachable to a circumferential wrapped portion thereof, the remote end of said second elastic band detachably attachable to a circumferential wrapped portion thereof, and the remote end of said third elastic band detachably attachable to a selected one of said first and second elastic bands.

* * * * *